United States Patent [19]

Genco et al.

[11] Patent Number: 4,679,917
[45] Date of Patent: Jul. 14, 1987

[54] DEVICE FOR MEASURING INTRAOCULAR LIGHT SCATTER

[75] Inventors: Louis V. Genco, Enon; Harry L. Task, Dayton, both of Ohio

[73] Assignee: The United States of America as represented by the Secretary of the Air Force, Washington, D.C.

[21] Appl. No.: 726,568

[22] Filed: Apr. 24, 1985

[51] Int. Cl.$^4$ .......................... A61B 3/10; A61B 3/02
[52] U.S. Cl. .................................. 351/221; 351/211; 351/243; 351/237
[58] Field of Search ................ 351/211, 221, 243, 237

[56] References Cited

U.S. PATENT DOCUMENTS

| | | |
|---|---|---|
| Re. 28,921 | 8/1976 | Haines et al. |
| 3,684,355 | 8/1972 | Molner ................................ 351/243 |
| 4,279,478 | 7/1981 | Matsumura. |
| 4,390,255 | 6/1983 | Nohda et al. |
| 4,421,391 | 12/1983 | Matsumura et al. |

Primary Examiner—Rodney B. Bovernick
Attorney, Agent, or Firm—Bobby D. Scearce; Donald J. Singer

[57] ABSTRACT

A novel optical device and method for measuring intraocular light scatter in a human vision system of a subject is described which comprises first and second light sources of respective predetermined intensities, the images of which are optically folded along a common optical axis and projected into the vision system of the subject, the first source being of intensity sufficient to generate intraocular haze in the vision system of the subject, the second source being movable in a plane substantially perpendicular to the axis along which its image is projected whereby the second source image as viewed by the subject may be selectively viewed with respect to the first source image to measure the apparent peripheral extent of the haze surrounding the first source image.

16 Claims, 4 Drawing Figures

DEVICE FOR MEASURING INTRAOCULAR LIGHT SCATTER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to devices for measuring visual functions of the human vision system, and more particularly to a device for measuring light scatter within the ocular media of a human vision system.

The ability to clearly detect objects in the visual field is affected by the presence of image-destroying light scatter within the ocular media. This light scattering and the observed intraocular haze generated thereby may be induced by particulates within the aqueous or vitreous humor or by changes in transparency of the cornea or lens. Injuries to the eye or surgical procedures involving the eye often temporarily increase intraocular haze, and recovery could be effectively monitored by ovserving light scattering characteristics of the eye. No existing device provides a suitably accurate means to measure intraocular light scatter in a noninvasive, self-administered test, and therefore, there exists a need for an optical device to accurately determine an individual's intraocular light scatter characteristics.

The present invention provides an optical system and associated method for measuring the halation or light spread induced within the ocular media of a human vision system, which may be caused by the presence of particulates or other light-scattering matter within the aqueous or vitreous humor, or which may result from changes in transparency of the cornea or lens of the eye due to trauma or the aging process. In the practice of the invention, images of a first light source (target), and a second light source (probe) are projected along respective intersecting orthogonal optical axes and combined by a beam splitter for viewing by a subject. The target light creates a visible halation ring in the presence of light scattering matter in the eye of the subject. The probe light may be configured to be movable in a plane perpendicular to its axis of projection so that the apparent position of the image of the probe light may be selectively positioned around and through the area defined by the halation ring of the target image to define the extent thereof. Probe and target light intensities may be selected so that the image of the probe light disappears when it enters the halation ring of the target. Measurement of the extent of the halation ring may be correlated with the scatter characteristics of the eye of the subject.

The invention is highly useful in the assessment of the physiological condition of the media of the eye. The optical device and measurement method described may be used for tracking the progress of cataracts and post surgical conditions of the eye (secondary cataracts), monitoring ocular trauma conditions or surgical or ophthalmic procedures, establishing baselines for research on visual functions, defining threshold values for glare susceptibility, determining effects of contact lenses or other refractive surfaces or elements on corneal physiology, and similar or related purposes. The measurement method of the present invention is noninvasive, and the optical device may be battery powered and otherwise configured to be portable.

It is, therefore, a principal object of the present invention to provide a novel method for measuring intraocular light scatter in a human vision system.

It is a further object of the invention to provide a novel device for measuring the intraocular light scatter coefficient in a human vision system.

These and other objects of the present invention will become apparent as the detailed description of certain representative embodiments thereof proceeds.

SUMMARY OF THE INVENTION

In accordance with the foregoing principles and objects of the present invention, a novel optical device and method for measuring intraocular light scatter in a human vision system of a subject is described which comprises first and second light sources of respective predetermined intensities, the images of which are optically folded along a common optical axis and projected into the vision system of the subject, the first source being of intensity sufficient to generate intraocular haze in the vision system of the subject, the second source being movable in a plane substantially perpendicular to the axis along which its image is projected whereby the second source image as viewed by the subject may be selectively viewed with respect to the first source mage to measure the apparent peripheral extent of the haze surrounding the first source image.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
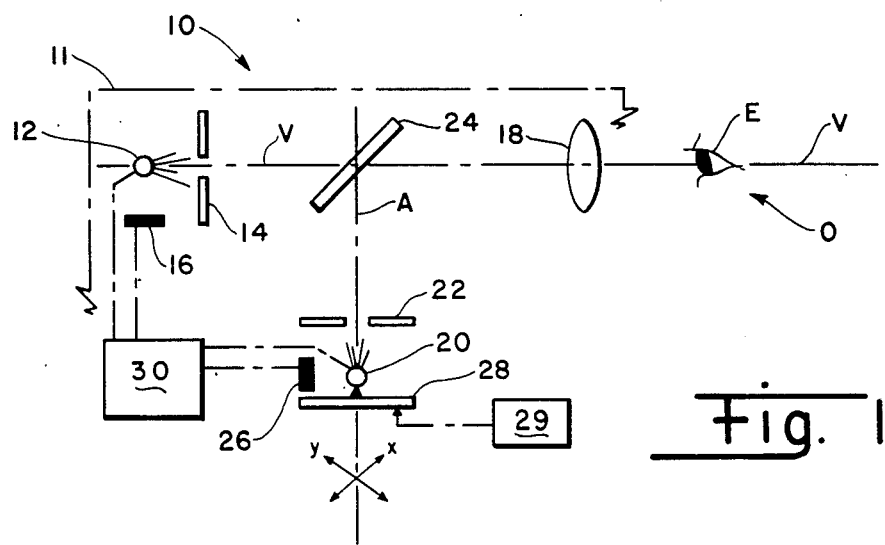
FIG. 1 is a schematic of a representative optical system for measuring intraocular light scatter in a human vision system according to the present invention.

Referring now to the accompanying drawings, FIG. 1 presents a schematic of a representative optical system 10 according to the present invention useful in testing a human vision system for intraocular light scatter. A first light source 12 of predetermined intensity and wavelength characteristics provides a first, stationary (with respect to viewing axis V) target for observation by a subject O. Light source 12 may comprise any conventional light source, such as an incandescent filament bulb, light emitting diode (LED), or the like, the same not being limiting of the invention herein. Source 12 preferably appears to subject O as a point source of light originating at optical infinity, and, accordingly, optics comprising a suitable collimating lens and/or spatial filter 14 may be provided to project a beam of light from source 12 along viewing axis V into the eye E of subject O. Light sensor 16 may be disposed near source 12 to measure the intensity of source 12 and to provide an output signal corresponding to the measured intensity. An image forming optical system 18, which may comprise one or a pair of eyepiece lenses, is disposed along viewing axis V through which subject O may view with one or both eyes light projected therethrough along viewing axis V. The intensity of light source 12 is maintained at sufficient level to cause a perceptible halation ring as viewed by subject O if observed through a media, viz., the aqueous or vitreous humor and cornea and lens of the eye of subject O, which is other than substantially totally transparent.

A second light source (probe light) 20 and associated collimating optics/spatial filter 22 are disposed along a second optical axis A which intersects viewing axis V orthogonally substantially as shown. A beam splitter/combiner 24 is disposed at the intersection of axes V,A in order to combine the image of probe light 20 projected along axis A with that of source 12 projected along axis V. Light source 20 may preferably have essentially the same wavelength characteristics as light source 12, and an intensity which is preferably a predetermined adjustable ratio of the intensity of light source 12; source 20 and opticsl/filter 22 are disposed along axis A in manner to provide a source of light also appearing to subject O as a point source originating at optical infinity. Light sensor 26 is disposed near source 20 to measure the intensity of source 20 and to provide an output signal corresponding to the measured intensity in like manner as light sensor 16. Light source 20 is attached to a movable x-y coordinate electromechanical positioning system 28 so that source 20 is selectively positionable in a plane perpendicular to axis A and defined by the plane of movement of mechanical x-y movement system 28. Position controller and sensing means 29 provides means to selectively position light source 20, and may be configured to be operable by subject O for allowing self-administered testing; controller/sensor 29 may include mechanical position transducers, electro optical position sensors, quadrature sensing system, or the like, for sensing the position of light source 20 in its plane of movement and may provide an output signal corresponding to the measured position of source 20 relative to axis A.

The absolute and relative intensities of each light source 12,20 are maintained at respective predetermined levels by suitable electronics/power source 30 connected by suitable electrical means to sources 12,20 and light sensors 16,26. System 10 may be otherwise configured whereby light sensors 16,26 provide controlling input signals to electronics/powr source 30 for maintaining light sources 12,20 at selected intensity levels.

Power source 30 may comprise battery power whereby system 10 is rendered portable, and the various components of system 10 may be sized accordingly for mounting within a compact housing 11 (shown schematically by peripheral broken line).

Figure 2:
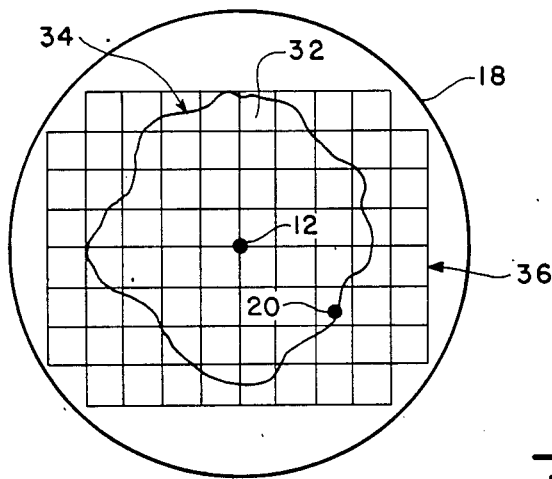
FIG. 2 is a diagram of the combined images of target and probe light sources generated in the method of the present invention for measuring intraocular light scatter.

In the use of optical system 10 to measure intraocular light scatter according to the method of the present invention, subject O may preferably first be preconditioned to a specific predetermined light intensity level. Subject O fixates on the image of light source 12 as viewed along axis V, and moves x-y system 28 (such as through controller/sensor 29) to cause the image of probe light 20 to pass through the area defining the zone of halation caused by light source 12. Reference is now made to FIG. 2 of the drawings which shows a diagram of the combined images of sources 12,20 as observed by subject O. Since light source 12 will, as suggested above, cause a zone 32 of halation or light scatter about its image as viewed along axis V in the presence of a light-scattering intraocular media, the image of probe light 20 (of appropriate predetermined intensity) will disappear when the intensity of halation zone 32 is sufficient to cause the image contrast of probe light 20 to fall below threshold. The apparent peripheral extent (circumference 34) of halation zone 32 may therefore be defined for any predetermined set of intensity levels for light sources 12,20 by suitable movement of x-y system 28 and corresponding positioning of probe light 20 within its plane of movement to observe the image thereof against halation zone 32.

Figure 3:
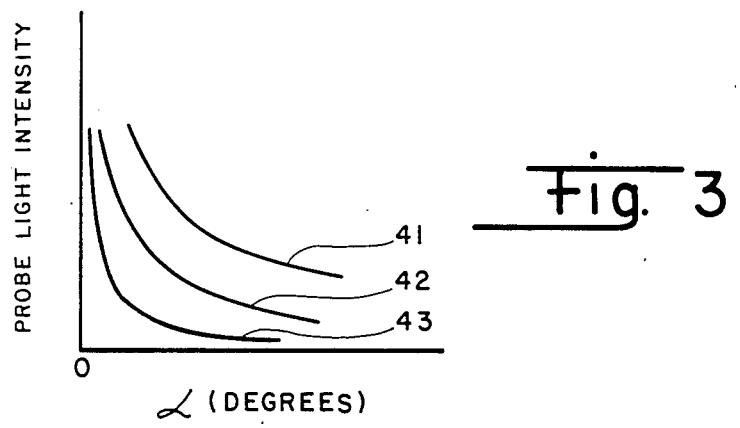
FIG. 3 presents representative graphs of probe light intensity (or probe light to target intensity ratio) versus visual angle between target source and probe light illustrating qualitatively various degrees of scatter in vision systems.

Circumference 34 of halation zone 32 is delineated by the isopter of equal scatter (isoscat of visible radiation). Depending on the amount of scatter or halation, these isopters will be more or less distant from the target source image. Eyepiece 18 may include a calibrated grid 36 or the like, and optical system 10 may otherwise be sized and calibrated, so that the angular subtent (or x-y relative location) of each measured point on the circumferential extent 34 of halation zone 32 defining the isoscat may be read directly from the instrument comprising system 10. The probe motion is continued until the entire zone of halation is plotted and the isoscat established. For most accurate and stable detection of the isoscat, the relative intensities of light sources 12,20 should be appropriately set, and the values corresponding to observed positions of probe 20 should be recorded as its image passes from invisible to visible. The procedure just described may be repeated for various target and probe light intensity ratios to generate a scatter profile or probe light intensity versus visual angle a between the target source and the probe light spot. The resulting profile for a subject may be represented by one of the profiles labeled 41,42,43 in FIG. 3, wherein a subject's vision as represented by profile 41 would be relatively poor as characterized by a high degree of scatter, whereas another subject's vision as represented by profile 43 would be relatively good as characterized by a low level of intraocular scatter.

Figure 4:
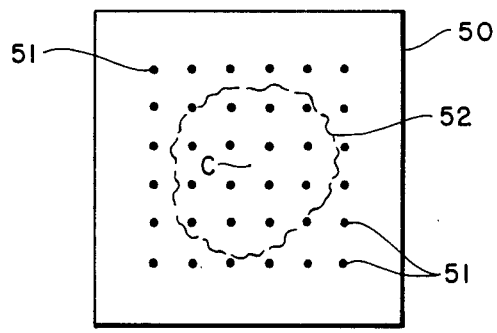
FIG. 4 illustrates an alternative configuration for the probe light source of the invention.

In an alternative embodiment, probe light source 20 may be replaced by a planar array 50 of substantially stationary point light sources 51 of predetermined spacing and individually controllable intensity, as shown in FIG. 4, the image of which array may be projected along axis A and folded onto the image of target source 12 for projection into the vision system of subject O. Source 12 (the image of which may be observed at C) may thereby define a halation zone 52 having an apparent peripheral extent 54 superimposed on the image of array 50 and being definable by subject O in terms of the position of zone 52 with respect to array 50 and/or calibrated grid 36 on eyepiece 18 of the system.

Each eye E of subject O may be measured separately, and (with a binocular eyepiece system) both eyes may be measured simultaneously in order to define respective monocular and binocular isoscats. The corresponding data may be compared to a set of standards to determine the degree of intraocular light scatter, and to compare the results to an average or norm for subject O. Larger isoscats indicate a greater number of scattering bodies, greater intraocular haze, and poorer visual performance. Appropriate mathematical treatment of data generated according to the method of the present invention may establish a model predictive of visibility for selected probe and target light source 12 intensities and set of ambient conditions.

The present invention therefore provides a novel device and method for measuring intraocular light scatter in a human vision system. It is understood that certain modifications to the invention as described may be made, as might occur to one with skill in the field of the invention, within the scope of the appended claims. Therefore, all embodiments contemplated hereunder which achieve the objects of the invention have not been shown in complete detail. Other embodiments may be developed without departing from the spirit of the invention or from the scope of the appended claims.

We claim:

1. An optical system for measuring intraocular light scatter in the vision system of a subject, comprising:
   a. a first glare source of light and a and second point source of light of respective preselected intensities, said first glare source being of intensity greater than said second point source whereby intraocular haze is generated by said first glare source in said vision system of said subject;
   b. first optical means for projecting an image of said first glare source along a first optical axis into said vision system of said subject;
   c. second optical means for projecting an image of said second point source along a second optical axis intersecting said first optical axis;
   d. means for optically superimposing said image of said second point source onto said image of said first glare source for projection therewith along said first optical axis into said vision system of said subject;
   e. means connected to said second point source for moving said second point source in a plane substantially perpendicular to said second optical axis, whereby said image of said second point source as viewed by said subject is selectively movable with respect to said image of said first glare source; and
   f. measurement means for gauging the observed circumferential extent of said haze in contrast to said image of said second point source.

2. The optical system as recited in claim 1 wherein said measurement means includes a calibrated optical eyepiece including a set of calibrated lines.

3. The optical system as recited in claim 1 wherein said first optical axis and said second optical axis are mutually orthogonal.

4. the optical system as recited in claim 1 wherein said means for optically superimposing said image of said second point source onto said image of said first glare source comprises an optical beam splitter.

5. The optical system as recited in claim 1 wherein the intensities of said first glare source and said second point source are in a preselected ratio.

6. An optical system for measuring intraocular light scatter in the vision system of a subject, comprising:
   a. a first glare light source of preselected intensity whereby intraocular haze is generated in said vision system of said subject;
   b. first optical means for projecting an image of said first glare source along a first optical axis into said vision system of said subject;
   c. a second light source comprising a plurality of substantially point sources of respective preselected intensities less than the preselected intensity of said first glare source, said point sources being arranged in a preseleced planar array with preselected spacing;
   d. second optical means for projecting an image of said second light source along a second optical axis intersecting said first optical axis;
   e. means for optically superimposing said image of said second light source onto said image of said first glare source for projection therewith along said first optical axis into said vision system of said subject; and
   f. measurement means for gauging the observed circumferential extent of said haze in contrast to said image of said second light source.

7. The optical system as recited in claim 6 wherein said measurement means includes a calibrated optical eyepiece including a set of calibrated lines.

8. The optical system as recited in claim 6 wherein said first optical axis and said second optical axis are mutually orthogonal.

9. The optical system as recited in claim 6 wherein said means for optically superimposing said image of said second light source onto said image of said first glare source comprises an optical beam splitter.

10. The optical system as recited in claim 6 further comprising means to control individually the respective intensities of said plurality of substantially point sources.

11. A method for measuring intraocular light scatter in the vision system of a subject, comprising the steps of:
   a. providing a first glare source of light and a second point source of light of respective preselected intensities, said first glare source being of intensity greater than said second point source whereby intraocular haze is generated by said first glare source in said vision system of said subject;
   b. projecting an image of said first glare source along a first optical axis into the vision system of said subject;
   c. projecting an image of said second point source along a second optical axis intersecting said first optical axis;
   d. optically superimposing said image of said second point source onto said image of said first glare source for projection therewith along said first optical axis into said vision system of said subject;
   e. selectively moving said second point source in a plane substantially perpendicular to said second optical axis and
   f. recording the observed positions of said image of said second point source relative to said image of said first glare source to define the circumferential extent of said haze within said vision system as observed by said subject.

12. The method as recited in claim 11 wherein said first optical axis and said second optical axis are mutually orthogonal.

13. The optical system as recited in claim 11 wherein the intensities of said first glare source and said second point source are in a preselected ratio.

14. A method for measuring intraocular light scatter in the vision system of a subject, comprising the steps of:
   a. providing a first glare light source of preselected intensity whereby intraocular haze is generaed in said vision system of said subject;
   b. projecting an image of said first glare source along a first optical axis into the vision system of said subject;

c. providing a second light source comprising a plurality of substantially point sources of respective preselected intensities less than the preselected intensity of said first glare source, said point sources being arranged in a preselected planar array with preselected spacing;

d. projecting an image of said second light source along a second optical axis intersecting said first optical axis;

e. optically superimposing said image of said second light source onto said image of said first glare source for projection therewith along said first optical axis into said vision system of said subject;

f. comparing said image of said second light source with said image of said first glare source; and g. recording points defining the cirumferential extent of said haze within said vision system relative to said planar array of said point sources as observed by said subject.

15. The method as recited in claim 14 wherein said first optical axis and said second optical axis are mutually orthogonal.

16. The method as recited in claim 14 comprising means to control individually the respective intensities of said plurality of substantially point sources.

* * * * *